United States Patent [19]
Kuhl et al.

[11] Patent Number: 4,775,629
[45] Date of Patent: Oct. 4, 1988

[54] APPARATUS FOR PROCESSING FLUIDS

[75] Inventors: Ernest B. Kuhl, Pennsville, N.J.; George R. Long, Newark; Juleen A. Mitchell, Wilmington, both of Del.; Richard S. Jenkins, Kennett Square, Pa.; Henry R. Wolfe, Jr., Newark, Del.; Gerard F. Malone, Marlton, N.J.

[73] Assignee: E. I. Du Pont de Nemours and Company, Wilmington, Del.

[21] Appl. No.: 45,628

[22] Filed: May 5, 1987

[51] Int. Cl.$^4$ ............................................. C12M 1/16
[52] U.S. Cl. .................................... 435/299; 435/311; 210/282; 222/507; 222/548
[58] Field of Search ............... 435/299, 298, 300, 296, 435/301, 287; 210/249, 282, 455, 248; 425/261; 222/507, 548; 251/155, 352; 422/101

[56] References Cited

U.S. PATENT DOCUMENTS

| 2,765,954 | 10/1956 | Wohler | 222/548 |
| 3,118,578 | 1/1964 | Collins | 222/548 |
| 3,567,029 | 3/1971 | Quame | 210/249 |
| 4,214,993 | 7/1980 | Forsythe, Jr. et al. | 210/455 |
| 4,380,257 | 4/1983 | Howell | 425/261 |

FOREIGN PATENT DOCUMENTS 210063 5/1966 Sweden ............................... 222/548

OTHER PUBLICATIONS

Automated On-Stream Syringeless Injection in HPLC, Kenneth C. van Horne and Thomas Good, American Laboratory, Oct. 1983.
Vacuum Manifold, Alltech Associates, Inc., Applied Science Labs, Catalog No. 100, pp. 506, 510 and 516, (1987).

Primary Examiner—James C. Yeung

[57] ABSTRACT

A cartridge is formed of two parts which form an outlet valve at the lower end. The valve is opened or closed by relative rotation of the parts.

9 Claims, 2 Drawing Sheets

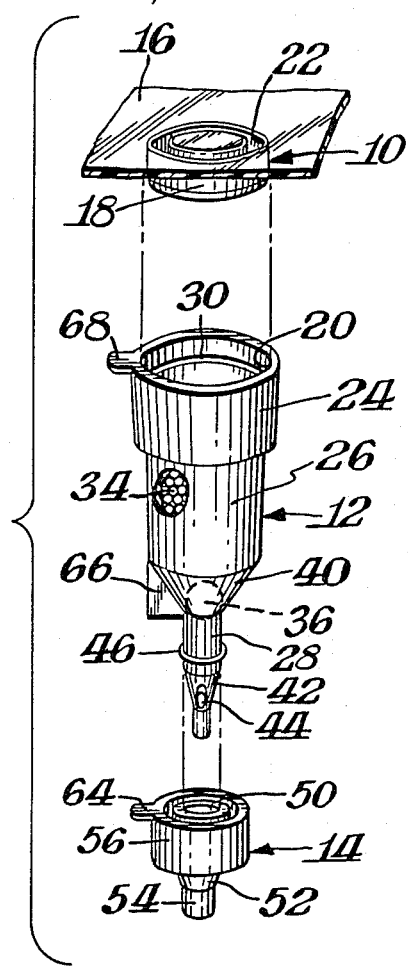
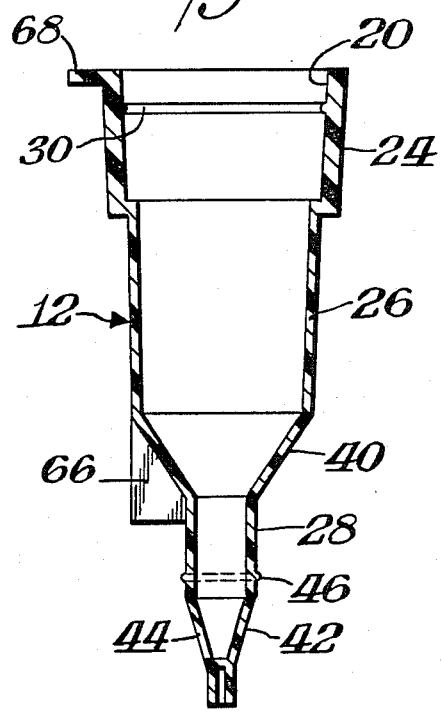
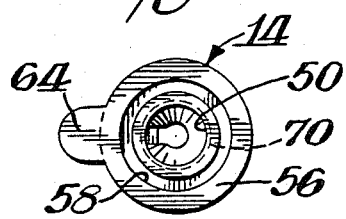
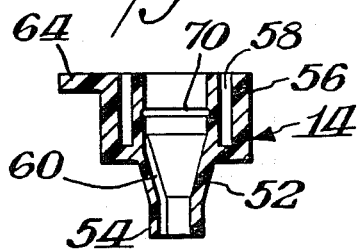

APPARATUS FOR PROCESSING FLUIDS

BACKGROUND OF THE INVENTION

This invention relates to a fluid processing apparatus and, more particularly, to an apparatus for use with chemical synthesizers.

It is often necessary in the biotechnology field to use support particles on which various biochemical reactions may take place. These particles may be various resins and typically may be polystyrene beads having a diameter in the range of 50–100 microns. Thus in the case of the synthesis of peptides, various amino acids must be linked together. When the amino acid chain contains 100 or more amino acids, it is called a protein. The chemical bond between two amino acids is an amide bond and is formed by the amine group from one amino acid combining with the carboxylic group of the next.

One of the synthesis techniques is to use a solid phase peptide synthesizer to add amino acid sequentially onto to an insoluble resin such as the polystyrene beads mentioned above. Synthesis begins with the attachment of the carboxylic end of an amino acid to the resin, and continues with one amino acid after another until the amino terminus of the desired peptide is reached. Various commercial resins are available for this purpose. The processing is usually accomplished in a non-disposable cartridge in which the various solvents and reagents necessary to the peptide synthesis are added to the cartridge, containing the beads, for each step of the synthesis process. After the reaction of each reagent is complete the reagent must be removed from the bead-containing cartridge, the beads washed, a new reagent added, etc. until the peptide synthesis process is complete. To speed the process it is preferable to remove the fluid reagents, solvents, etc. by applying a vacuum to the lower end of the cartridge.

The application of vacuum is similar to the techniques used in separating techniques using stationery beads using chromatographic techniques. Among such vacuum separators of the prior art is that described by Quame in U.S. Pat. No. 3,567,029. Quame describes the use of a disposable separating column filled with a particular solid phase, capable of extracting certain lipophilic compounds, including the most commonly encountered, abused drugs, such as phenobarbital, amphetamine, methadone and the like. In a typical drug extraction, such as from a urine sample, Quame allows the urine sample to pass through the column. The column selectively adsorbs any lipophilic drugs contained in the urine, thereby extracting the lipophilic drugs contained in the urine. Next, the adsorbed drugs are eluted from the column by a solvent and any residual aqueous phase is retained by a filter.

Another separating cartridge of this type is described by Forsythe, Jr., et al. in U.S. Pat. No. 4,214,993 which describes a three-piece cartridge including a cap, an extraction housing, a separating column, and a primary recovery cup. A secondary recovery cup may also be nested onto the lower end of the waste cup. The primary recovery cup has interior flanges for positioning and protecting the bottom end of the column against damage. Each of the elements has an enlarged upper portion forming an exterior step which facilitates mounting in the swinging bucket of a centrifuge. The column itself may comprise particles of a suitable separatory material with the top and the bottom of the particles retained by porous supports.

The Howell patent, U.S. Pat. No. 4,380,257, describes the use of a vacuum to increase the speed with which a fluid is withdrawn from the column. Another vacuum cartridge separation technique is described in an article entitled *Automated On-Stream Syringeless Injection in HPLC*, Kenneth C. Van Horne and Thomas Good, American Laboratory, October 1983.

These cartridges of the prior art do not meet all the needs of some of the biotechnology processing required particularly in the case of peptide synthesis. In this latter application, it is necessary (a) to mechanically agitate the cartridge to incur mixing; and (b) to facilitate the opening and the closing of the cartridge. Only when it is desired to regulate the application of the vacuum to remove the reagent need the cartridge be open. No provision is made in these prior cartridges to close the lower end other than by the use of an end cap. This is not convenient for use in synthesis operations where the cartridge must be opened and closed many times. It is necessary that the cartridge be closed during mixing of the reagents to prevent the leakage of fluid from the cartridge during the agitation period.

SUMMARY OF THE INVENTION

Many of the disadvantages of these prior art mixing cartridges are alleviated by the subject invention. The invention is an apparatus for processing fluids having a cartridge with an enlarged middle portion adapted to receive support particles and a tubular lower portion communicating with the middle portion and having an outlet at its bottom end, the middle portion being tapered inward toward its lower end to join the lower portion of the cartridge, a closure member insertable into the top end of the cartridge, and a cap-like insert frictionally engaging the bottom end of the lower portion, the cartridge having a longitudinal axis, the improvement wherein: the insert is cylindrical, annularly fits over the lower portion, and has a discharge tip at its lower end, the tubular portion and insert being in frictional rotational engagement, each defining radial passageways which may be aligned by relative rotation therebetween about the cartridge axis to provide a fluid path between the cartridge lower portion and the discharge tip of the insert.

In a preferred embodiment, the insert includes an exterior cylindrical portion annularly disposed relative to the insert and secured by a radial web to the lower end of the insert. Also, the cartridge lower portion and insert lower end are each defined by inwardly tapered mating tubes, the passageways being located along the taper of each. The passageway in the insert is defined by a longitudinal groove in the interior wall of the insert communicating with the discharge tip. Also, the cartridge defines a radial tab located at the radial position of the cartridge passageway. The cartridge lower portion defines a raised, exterior annular ring adapted more tightly to engage the insert. The inside of the insert defines an annular groove adapted to engage the cartridge ring to provide a good seal.

BRIEF DESCRIPTION OF THE DRAWINGS

Further advantages and features of this invention will become apparent from the following description wherein:

FIG. 1 is an exploded pictorial view of the cartridge of this invention wherein the cap is a portion of a cap sheet;

FIG. 2 is a cross sectional side elevation view of the cartridge of FIG. 1;

FIG. 3 is a cross sectional side elevation view of the insert of FIG. 1;

FIG. 4 is a plan view of the cartridge of FIG. 3;

The cartridge which forms a heart of the fluid processing apparatus of this invention is depicted most clearly in FIGS. 1-4. This cartridge is adapted to contain particles which provide a solid support for the chemical reactions to take place. The cartridge may be insertable into the receptacles of a shaking apparatus to facilitate mixing of the cartridge reagents. By rotating the top half of the cartridge relative to the insert, a valve in the bottom of the cartridge may be opened or closed to permit the reagents or solvents in the cartridge to be removed. Such removal is accomplished preferably by the application of vacuum to speed up the fluid flow from the cartridge.

Figure 5:
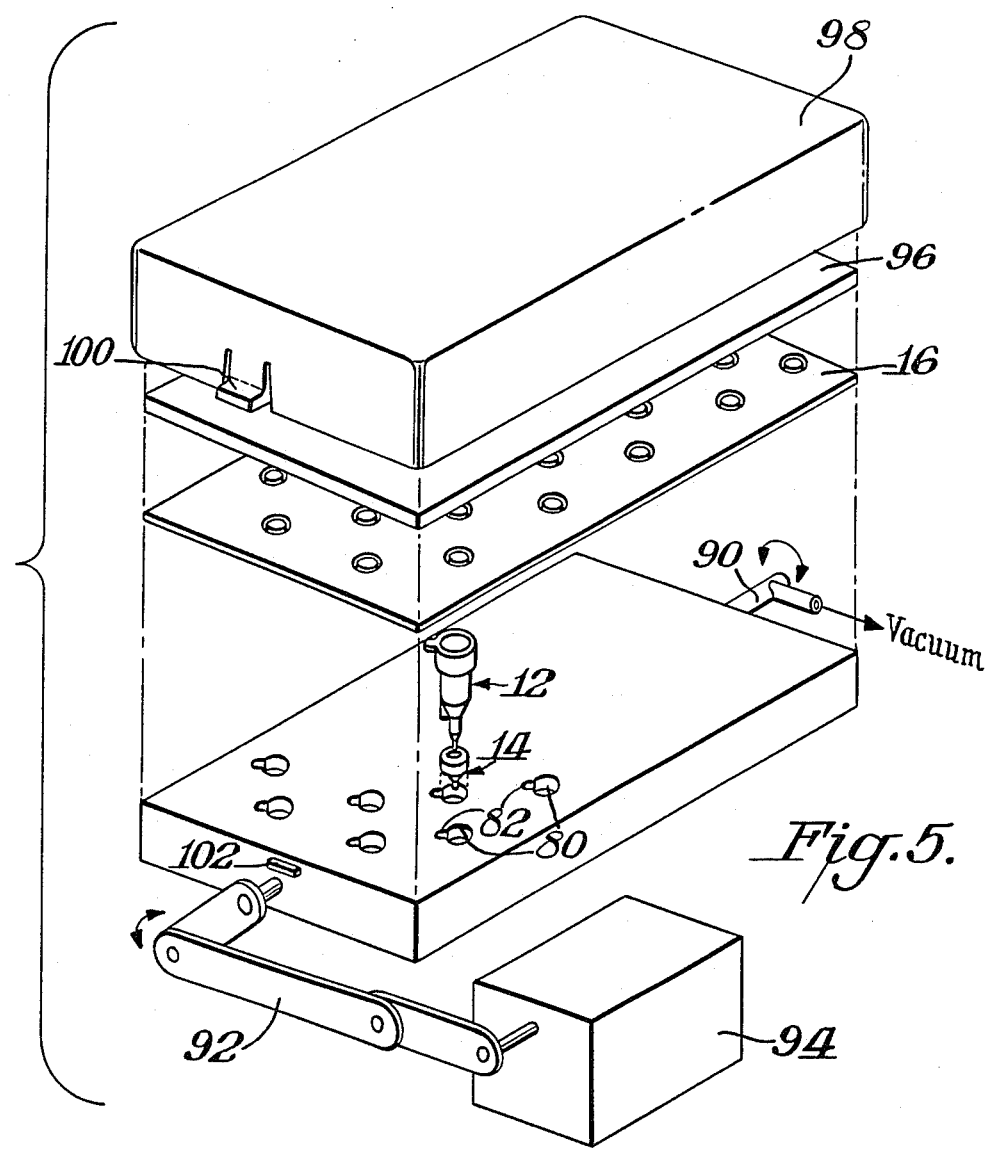
FIG. 5 is a pictorial exploded representation of a peptide synthesizer at which plural cartridges of type depicted in FIG. 1 are used.

As is seen, particularly in FIG. 1, the cartridge consists of three parts: A cap 10, a particulate chamber 12, and a valve insert 14. Typically the cap 10 is formed integrally with a cap sheet 16 which, as may be seen more clearly in FIG. 5, is simply a sheet of plastic with a plurality of caps 10 formed therein. The sheet and the cap, as may the other parts of the cartridge, be formed of a suitable plastic such as polypropylene. This is preferred due to the corrosive natures of the various chemistries involved. Each cap 10 is formed, as noted in the cap sheet 16, to have a cylindrical portion 18 adapted to fit into the top end 20 of the particulate chamber 20. To permit this construction an annular recess 22 may be formed in the cap sheet to facilitate the molding operation.

The particulate chamber 12 comprises a top end 24, a middle portion 26, and a lower portion 28. The top end 24 has formed on the inner wall a raised annular ring 30 (FIG. 5) to provide a tight engagement of the cap 10 with the particulate chamber 12 so that it is securely sealed and the cartridge is supported by, and may be lifted by, the cap sheet 16. The middle portion 26, of slightly reduced diameter, is adapted to contain the support particles 34. The particles are retained in the middle portion 26 by a porous filter 36 which may be in the form of a ball. The middle portion 26 is tapered inwardly as at 40 toward the lower portion 28. The lower portion 28 is tubular and is further tapered inwardly at the lower end as at 42 and is formed to have a radial aperture 44 and an external radial retention ring 46. The lower taper 42 is closed at the lower end so that the only outlet for the particulate chamber 12 is through the radial orifice or passageway 44.

Finally, valve insert 14 is formed to fit over the lower portion 28 of the chamber 12 in a mating relationship. Thus, it is formed to have a cylinder 50 defining an internal bore which can engage the lower portion 28 and is tapered as at 52 to conform to the taper 42 of the chamber 12 and finally is provided with an open discharge tip 54. An exterior cylindrical portion 56 is formed about the cylinder 50 and is attached as by a web 58 at the lower end so that the cylindrical portion 56 may flex to some extent relative to the cylinder 50. To complete the insert 14, a radial passageway 60 is formed by a longitudinal groove along the interior of the discharge tip and the tapered portion 52 so that fluid from the orifice 44 may pass along the passageway 60 and out the discharge tip 54. This may occur only when the valve formed by the valve insert and chamber 12 is open, i.e., when the orifice 52 and the passageway 60 are in alignment by relative rotation between the valve insert 14 and the chamber 12.

Finally, an exterior tab 64 is formed on the cylindrical portion 56 at a peripheral position corresponding to that of the passageway 60. This is used, as will be described, to position the valve insert 14 and prevent its rotation when mounted in the vacuum mounting plate (FIG. 5). A similar but longitudinally positioned tab 66 is positioned on the taper 36 of the chamber 12 and is in peripheral alignment with the orifice 44. A further alignment tab 68 is formed on the upper portion of the chamber 12. Thus, when the tab 64 is in alignment with tabs 66 and 68, the valve formed by the valve insert 14 and the particular chamber 12 is open when they are not in alignment sufficiently the valve is closed.

Finally, an interior groove 70 is formed in the insert and is adapted to engage the retentioning ring 46 of the chamber 12 so that essentially a vacuum seal is provided together with a secure connection between the insert and the chamber.

Figure 6:
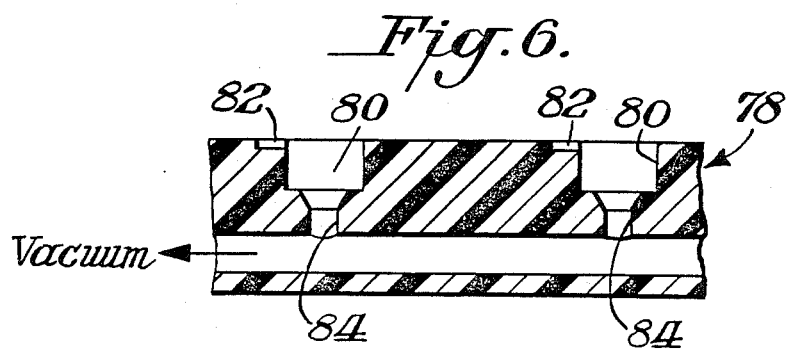
FIG. 6 is a fragmentary side elevation view cutaway to depict the vacuum lines.

The cartridge is adapted to fit into a synthesizer apparatus which is most clearly seen in FIG. 6. As is seen in FIG. 6, the apparatus includes a plate having plural receptacles 80. Each receptacle 80 has a side recess on notch 82 to accommodate the tab 64 and is connected through a passageway 84 to a vacuum line 86. The vacuum line may be connected through a tube 90 to a source of vacuum. The plate is also adapted to be driven by a mechanical linkage 92 coupled to a drive motor 94 such that upon rotation of the drive motor 94 the linkage 92 causes the vacuum plate to be rocked back and forth through approximately 130° angle. The vacuum plate may be constructed of polypropylene, polyethylene, or Teflon ®. To complete the assembly, the cap sheet 16 is used with a foam sheet 96 both of which are housed within a cover 98 which has a snap connector 100 on either end adapted to engage a slot 102 on the vacuum mounting plate such that when the cartridges are inserted in the receptacles they may be engaged by appropriate cap of the cap sheet and held in position by the cover which is snapped over the vacuum plate.

Thus, in a typical single step of the operating procedure of a peptide synthesis, the desired reagents which are to be mixed or washed are placed in the desired cartridge. The cartridge is placed in the appropriate receptacle in the vacuum plate and the cap sheet attached. Alternatively, the cartridge may be attached to the cap sheet before positioning within the vacuum plate. Care must be taken to insure that the tab 64 of the valve insert be positioned in the appropriate notch 82 to prevent its rotation. This is usually accomplished with all of the tabs in alignment so that the valve is closed. Next, the foam and cover are placed over the cartridges and the cover snapped into place. The motor is actuated such that the rocking motion may begin. After this is completed, the cover is snapped off by releasing the snaps 100. The cap sheet 16 may be removed from the receptacles by pulling the cap sheet back. Then, as needed, the valves may be opened by rotation of the top portion of each cartridge so that the tabs are no longer in alignment. Vacuum may be applied and the fluid removed from the cartridge. This operation may be repeated as often as is necessary to complete the synthesis operation.

What is claimed:

1. An apparatus for processing fluids having a cartridge with an enlarged middle portion adapted to receive support particles and a tubular lower portion communicating with the middle portion and having an outlet at its bottom end, the middle portion being tapered inward toward its lower end to join the lower portion of the cartridge, and a closure member insertable into the top end of the cartridge having a longitudinal axis, the improvement wherein:

the insert is cylindrical, annularly fits over the lower portion, and has a discharge tip at its lower end, the tubular portion and insert being in frictional rotational engagement, each defining radial passageways which may be aligned by relative rotation therebetween about the cartridge axis to provide a fluid path between the cartridge lower portion and the discharge tip of the insert, the insert including an exterior cylindrical portion annularly disposed relative to the insert and secured by a radial web to the lower end of the insert the cartridge lower portion and insert lower end each being defined by inwardly tapered mating tubes, the passageways being located along the taper of each.

2. The apparatus as set forth in claim 1 wherein the passageway in the insert is defined by a longitudinal groove in the interior wall of insert communicating with the discharge tip.

3. An apparatus for processing fluids having a cartridge with an enlarged middle portion adapted to receive support particles and a tubular lower portion communicating with the middle portion and having an outlet at its bottom end, the middle portion being tapered inward toward its lower end to join the lower portion of the cartridge, and a closure member insertable into the top end of the cartridge having a longitudinal axis, the improvement wherein:

the insert is cylindrical, annularly fits over the lower portion, and has a discharge tip at its lower end, the tubular portion and insert being in frictional rotational engagement, each defining radial passageways which may be aligned by relative rotation therebetween about the cartridge axis to provide a fluid path between the cartridge lower portion and the discharge tip of the insert, the insert including an exterior cylindrical portion annularly disposed relative to the insert and secured by a radial web to the lower end of the insert, the cartridge lower portion and insert lower end each being defined by tubes with mating inward tapers, the passageways being located along the taper of each.

4. The apparatus as set forth in claim 3 wherein the cartridge defines a radial tab located at the radial position of the cartridge passageway.

5. The apparatus as set forth in claim 4 wherein the insert defines a radial tab located at the radial position of the insert passageway.

6. The apparatus as set forth in claim 4 wherein the cartridge lower portion defines a raised, exterior annular ring adapted more tightly to engage the insert.

7. The apparatus as set forth in claim 6 wherein the inside of the insert defines an interior annular groove adapted to engage the cartridge ring to provide a good seal.

8. The apparatus as set forth in claim 3 wherein the insert defines a radial tab located at the radial position of the insert passageway.

9. The apparatus as set forth in claim 8 wherein the closure member is integrally formed in a sheet containing additional closure members formed therein.

* * * * *